US010150741B1

(12) United States Patent
Wang et al.

(10) Patent No.: US 10,150,741 B1
(45) Date of Patent: Dec. 11, 2018

(54) METHOD FOR PREPARING AZOXYSTROBIN INTERMEDIATES

(71) Applicant: CAC Nantong Chemical Co., LTD, Nantong (CN)

(72) Inventors: Haishui Wang, Shanghai (CN); Binglian Yang, Shanghai (CN); Simian Xie, Shanghai (CN); Xiaohong Tian, Shanghai (CN); Jiwang Xu, Nantong (CN)

(73) Assignee: CAC Nantong Chemical Co., LTD, Nantong (CN)

( * ) Notice: Subject to any disclaimer, the term of this patent is extended or adjusted under 35 U.S.C. 154(b) by 0 days.

(21) Appl. No.: 15/869,186

(22) Filed: Jan. 12, 2018

(30) Foreign Application Priority Data

Oct. 31, 2017 (CN) .......................... 2017 1 1049390

(51) Int. Cl.
*C07D 239/34* (2006.01)

(52) U.S. Cl.
CPC .................................. *C07D 239/34* (2013.01)

(58) Field of Classification Search
CPC .................................................... C07D 239/34
See application file for complete search history.

(56) References Cited

U.S. PATENT DOCUMENTS 9,556,128 B2 * 1/2017 Deng .................... C07C 67/327

FOREIGN PATENT DOCUMENTS

CN 1062139 A 6/1996
CN 102311392 A 1/2012

* cited by examiner

*Primary Examiner* — Emily A Bernhardt
(74) *Attorney, Agent, or Firm* — Dilworth IP, LLC

(57) ABSTRACT

The present invention provides a method for preparing azoxystrobin intermediates, comprising reacting compound A and dichloropyrimidine in the presence of a trimethylamine catalyst with the addition of a sodium methoxide solution in methanol or the addition of sodium methoxide and methanol separately to produce a mixture of compound B and compound C. Azoxystrobin intermediate compound B and compound C are synthesized from compound A in the present invention, which is catalyzed by using a trimethylamine catalyst, allowing the reaction to have high efficiency and high yield. In addition, the trimethylamine catalyst has a low boiling point and thus can be easily recycled so that the ammoniacal nitrogen content in wastewater can be reduced, and the difficulties and high costs for wastewater processing can be also reduced. The recycled trimethylamine catalyst can be reused in preparing intermediate compound B, which also has a high catalytic effect and can also achieve a high product yield. The method of the present invention has significant synthetical cost advantages and is suitable for industrial production.

10 Claims, No Drawings

METHOD FOR PREPARING AZOXYSTROBIN INTERMEDIATES

TECHNICAL FIELD

The present invention belongs to the technical field of compound synthesis and relates to a method for preparing azoxystrobin intermediates.

BACKGROUND OF THE INVENTION

Azoxystrobin is a broad-spectrum and high-efficient fungicide product used in agriculture, which has the world's largest sales at present and is widely produced and used. Synthesises of compound B and compound C, which are key intermediates of azoxystrobin, are generally performed by a ring-opening and etherification reaction of benzofuranone (compound A) with 4,6-dichloropyrimidine in sodium methoxide/methanol solution.

At present, a majority of domestic enterprises adopt the method as disclosed in CN1062139A, i.e. adding sodium methoxide directly to initiate a ring-opening and etherification reaction and thus synthesizing a mixture of compounds B and C from compound A without adding any catalyst, which has the route as following:

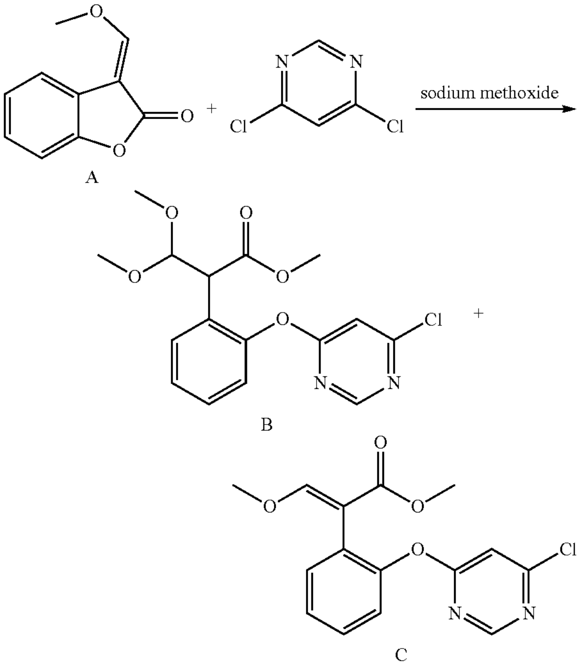

A

B

C

However, the yield of the method disclosed in CN1062139A can only be maintained at about 60-70% and a large number of by-products are produced in this reaction, which directly affects the purification of product in subsequent steps.

Another preparation method is synthesizing a mixture of compound B and compound C from compound A by using the catalyst DABCO as disclosed in CN102311392A. However, such catalyst is expensive, and has a high boiling point and thus is difficult to recycle, resulting in a high ammoniacal nitrogen content in wastewater, difficulties and high costs of wastewater processing and disadvantages for environmental protection and energy saving, although DABCO can improve the reaction rate as a catalyst.

Therefore, a low-cost and high-efficient method for preparing azoxystrobin key intermediate compound B and compound C is desired in the art, in which method the catalyst can be easily recycled and the ammoniacal nitrogen content in wastewater can be reduced.

SUMMARY OF THE INVENTION

In view of the deficiencies of the prior art, the object of the present invention is to provide a method for preparing azoxystrobin key intermediates. Trimethylamine is used in the method as a catalyst, which greatly increases the reaction rate and the product yield. In addition, the catalyst has a low boiling point and thus can be easily recycled, reducing the ammoniacal nitrogen content in the synthetic wastewater, being environmentally friendly and high-efficient and significantly reducing the cost for production.

The following technical solutions are adopted by the present invention to achieve the object.

The present invention provides a method for preparing azoxystrobin intermediates, comprising: reacting compound A and dichloropyrimidine in the presence of a trimethylamine catalyst with the addition of a sodium methoxide solution in methanol or the addition of sodium methoxide and methanol separately to produce a mixture of azoxystrobin intermediate compound B and compound C, with a reaction equation as following:

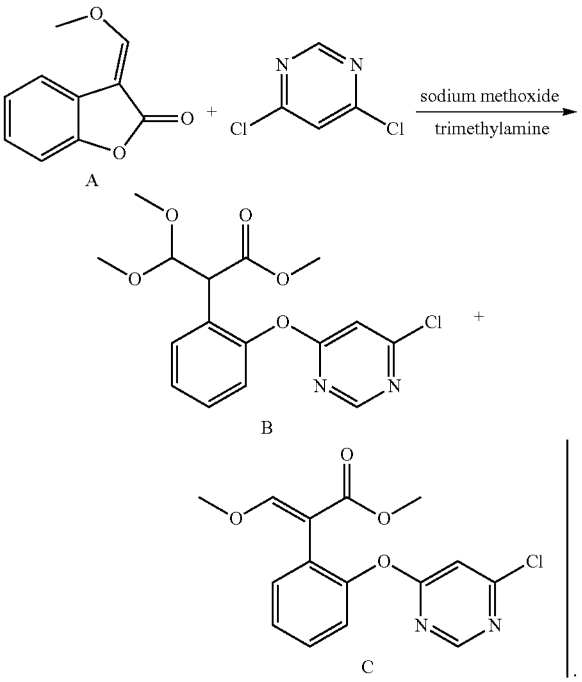

A

B

C

In the present invention, the trimethylamine catalyst is used to catalyze the synthesis of a mixture of azoxystrobin key intermediate compound B and compound C from compound A and dichloropyrimidine, greatly accelerating the reaction and increasing the product yield. In addition, the trimethylamine catalyst has a low boiling point and thus can be easily recycled, reducing the ammoniacal nitrogen content in the synthetic wastewater and the difficulties in wastewater processing, which is beneficial for environmental protection and significantly reduces the costs for production and post-processing. Moreover, the recycled trimethylamine catalyst can be reused, which also has a high catalytic effect and also achieves a high product yield.

Preferably, the trimethylamine catalyst is trimethylamine, a trimethylamine solution, or a salt of trimethylamine That is, in the present invention, the trimethylamine can be pure trimethylamine (i.e. trimethylamine which is in the form of gas at normal temperature and pressure), and can also be a trimethylamine solution or a salt forming from trimethylamine, in which the trimethylamine functions as a catalyst. Trimethylamine in various forms can be used, such as in forms of gas, solution and salt, which has good catalytic effect.

Preferably, the trimethylamine solution is any one selected from the group consisting of a trimethylamine solution in water, a trimethylamine solution in methanol, a trimethylamine solution in ethanol, a trimethylamine solution isopropanol, a trimethylamine solution in toluene and a trimethylamine solution in xylene, or a combination of at least two selected therefrom.

Preferably, the salt of trimethylamine is any one selected from the group consisting of trimethylamine hydrochloride, trimethylamine sulfate and trimethylamine methanesulfonate, or a combination of at least two selected therefrom.

The present inventor has surprisingly found that trimethylamine can be used as a catalyst in preparing a mixture of azoxystrobin intermediate compound B and compound C, which can not only increase the yields of intermediate compound B and compound C but also allow the trimethylamine in wastewater to be easily recycled and reused when the reaction is over, thus reducing the ammoniacal nitrogen content in wastewater, which has significant synthetical economic advantages.

In the present invention, the trimethylamine catalyst is taken out by heating and bubbling with nitrogen in the wastewater after preparation and absorbed by using methanol to obtain a trimethylamine solution in methanol. The recovered trimethylamine solution in methanol can be reused to catalyze the synthesis of a mixture of azoxystrobin key intermediate compound B and compound C from compound A and dichloropyrimidine. The ammoniacal nitrogen content in wastewater can be reduced from 300 ppm to 20 ppm or less, and the recovery rate of trimethylamine can reach 90% or more by adopting the recycling method. The present invention solves the problems including the difficulty of recycling, the high ammoniacal nitrogen content in wastewater, the difficulties and high costs for wastewater processing which are resulting from the high boiling point of DABCO.

Preferably, the molar ratio of compound A to the trimethylamine catalyst is 1:0.002-0.05, for example 1:0.002, 1:0.004, 1:0.006, 1:0.008, 1:0.01, 1:0.03, 1:0.05, etc.

Preferably, the molar ratio of compound A to dichloropyrimidine is 1:(1-1.4), for example 1:1, 1:1.05, 1:1.1, 1:1.2, 1:1.25, 1:1.3, 1:1.35 or 1:1.4.

Preferably, the reaction is performed at a temperature of from −20° C. to 30° C., for example −20° C., −15° C., −10° C., −5° C., 0° C., 5° C., 10° C., 15° C., 20° C., 25° C. or 30° C., preferably from 0 to 30° C.

Preferably, the reaction is performed for 1-10 h, for example 1 h, 2 h, 3 h, 4 h, 5 h, 6 h, 7 h, 8 h, 9 h or 10 h.

As a preferred technical solution, the preparation method of the present invention is: reacting compound A and dichloropyrimidine in the presence of a trimethylamine catalyst with the addition of a sodium methoxide solution in methanol or the addition of sodium methoxide and methanol separately at a temperature of from −20° C. to 30° C. to provide a mixture of azoxystrobin intermediate compound B and compound C, in which the molar ratio of compound A to the trimethylamine catalyst is 1:(0.002-0.05) and the molar ratio of compound A to dichloropyrimidine is 1:(1-1.4).

Compared with the prior art, the present invention has the following benefits:

Azoxystrobin intermediate compound B and compound C are synthesized from compound A in the present invention, which is catalyzed by using a trimethylamine catalyst, allowing the yield of the mixture of compound B and compound C to be up to 85% and may even be 90% or more and allowing the reaction to have high efficiency and high yield. In addition, the trimethylamine catalyst has a low boiling point and thus can be easily recycled so that the ammoniacal nitrogen content in water can be reduced to 20 ppm or less, and the recycling rate of trimethylamine can be up to 90% or more, solving the problems including the difficulty of recycling, the high ammoniacal nitrogen content in wastewater, the difficulties and high costs for wastewater processing which are resulting from the high boiling point of DABCO catalyst. The recycled trimethylamine catalyst can be reused in preparing intermediate compound B and compound C, which also has a high catalytic effect and can also achieve a high product yield. Using a trimethylamine catalyst to catalyze the synthesises of azoxystrobin intermediate compound B and compound C from compound A allow the reaction to be high-efficient and reduce the production cost. The method of the present invention has significant synthetical economic advantages and is suitable for industrial production.

DETAILED DESCRIPTION OF THE INVENTION

The technical solutions of the present invention are further described below by using specific embodiments. It should be understood by those skilled in the art that the examples are merely to help understand the present invention and should not be construed as a specific limitation to the present invention.

The contents of the raw materials or products are represented by mass percentages in the following examples.

Example 1

49.3 g of compound A (98%, 0.274 mol), 44.8 g of dichloropyrimidine (98.5%, 0.296 mol), and 203 ml of toluene were added sequentially into a 500 mL three-neck flask, stirred uniformly at room temperature. 0.42 g (having a content of 30%, 0.00213 mol) of a trimethylamine solution in methanol was further added, cooled to 5° C. with stirring, at which point 55 g (28.87%, 0.294 mol) of a sodium methoxide solution in methanol was added drop-wise, controlling the addition time to be 5 h, and incubated at 5° C. for 1 h after the addition. 2% hydrochloric acid was added to acidize the mixture to pH=1 after the incubation. The mixture was then washed twice by stirring with water and desolventized to obtain 80 g of a crude product of compound B and compound C. Determined by an internal standard method with HPLC, the ratio of compound B to compound C in the crude product was 70:10 and the yield of the mixture of compound B and compound C was 90%.

Example 2

49.3 g of compound A (98%, 0.274 mol), 44.8 g of dichloropyrimidine (98.5%, 0.296 mol), and 203 ml of toluene were added sequentially into a 500 mL three-neck flask, stirred uniformly at room temperature. 0.336 g (having a content of 30%, 0.0017 mol) of a trimethylamine solution in methanol was further added, cooled to 5° C. with stirring, at which point 55 g (28.87%, 0.294 mol) of a sodium methoxide solution in methanol was added drop-wise, controlling the addition time to be 5 h, and incubated at 5° C. for 1 h after the addition. 2% hydrochloric acid was added to acidize the mixture to pH=1 after the incubation. The mixture was then washed twice by stirring with water and desolventized to obtain 76 g of a crude product of compound B and compound C. Determined by an internal standard method with HPLC, the ratio of compound B to compound C in the crude product was 67:8 and the yield of the mixture of compound B and compound C was 85%.

Example 3

49.3 g of compound A (98%, 0.274 mol), 44.8 g of dichloropyrimidine (98.5%, 0.296 mol), and 203 ml of toluene were added sequentially into a 500 mL three-neck flask, stirred uniformly at room temperature. 0.207 g (having a content of 98%, 0.00213 mol) of trimethylamine hydrochloride was further added, cooled to 5° C. with stirring, at which point 55 g (28.87%, 0.294 mol) of a sodium methoxide solution in methanol was added drop-wise, controlling the addition time to be 5 h, and incubated at 5° C. for 1 h after the addition. 2% hydrochloric acid was added to acidize the mixture to pH=1 after the incubation. The mixture was then washed twice by stirring with water and desolventized to obtain 78.5 g of a crude product of compound B and compound C. Determined by an internal standard method with HPLC, the ratio of compound B to compound C in the crude product was 66:13 and the yield of the mixture of compound B and compound C was 89%.

Example 4

49.3 g of compound A (98%, 0.274 mol), 44.8 g of dichloropyrimidine (98.5%, 0.296 mol), and 203 ml of toluene were added sequentially into a 500 mL three-neck flask, stirred uniformly at room temperature. 0.504 g (having a content of 30%, 0.00255 mol) of a trimethylamine solution in methanol was further added, cooled to 5° C. with stirring, at which point 55 g (28.87%, 0.294 mol) of a sodium methoxide solution in methanol was added drop-wise, controlling the addition time to be 5 h, and incubated at 5° C. for 1 h after the addition. 2% hydrochloric acid was added to acidize the mixture to pH=1 after the incubation. The mixture was then washed twice by stirring with water and desolventized to obtain 79.6 g of a crude product of compound B and compound C. Determined by an internal standard method with HPLC, the ratio of compound B to compound C in the crude product was 70:10 and the yield of the mixture of compound B and compound C was 89%.

Example 5

49.3 g of compound A (98%, 0.274 mol), 44.8 g of dichloropyrimidine (98.5%, 0.296 mol), and 203 ml of toluene were added sequentially into a 500 mL three-neck flask, stirred uniformly at room temperature. 0.42 g (having a content of 30%, 0.00213 mol) of a trimethylamine solution in methanol was further added, cooled to 10° C. with stirring, at which point 55 g (28.87%, 0.294 mol) of a sodium methoxide solution in methanol was added drop-wise, controlling the addition time to be 5 h, and incubated at 10° C. for 1 h after the addition. 2% hydrochloric acid was added to acidize the mixture to pH=1 after the incubation. The mixture was then washed twice by stirring with water and desolventized to obtain 77.2 g of a crude product of compound B and compound C. Determined by an internal standard method with HPLC, the ratio of compound B to compound C in the crude product was 66:13 and the yield of the mixture of compound B and compound C was 86%.

Example 6

49.3 g of compound A (98%, 0.274 mol), 41.47 g of dichloropyrimidine (98.5%, 0.274 mol), and 203 ml of toluene were added sequentially into a 500 mL three-neck flask, stirred uniformly at room temperature. 0.11 g (having a content of 30%, 0.000548 mol) of a trimethylamine solution in methanol was further added, cooled to 5° C. with stirring, at which point 55 g (28.87%, 0.294 mol) of a sodium methoxide solution in methanol was added drop-wise, controlling the addition time to be 5 h, and incubated at 10° C. for 10 h after the addition. 2% hydrochloric acid was added to acidize the mixture to pH=1 after the incubation. The mixture was then washed twice by stirring with water and desolventized to obtain 81.2 g of a crude product of compound B and compound C. Determined by an internal standard method with HPLC, the ratio of compound B to compound C in the crude product was 72:12 and the yield of the mixture of compound B and compound C was 90%.

Example 7

49.3 g of compound A (98%, 0.274 mol), 58.1 g of dichloropyrimidine (98.5%, 0.384 mol), and 203 ml of toluene were added sequentially into a 500 mL three-neck flask, stirred uniformly at room temperature. 2.7 g (having a content of 30%, 0.0137 mol) of a trimethylamine solution in methanol was further added, cooled to 5° C. with stirring, at which point 55 g (28.87%, 0.294 mol) of a sodium methoxide solution in methanol was added drop-wise, controlling the addition time to be 5 h, incubated at 30° C. for 1 h after the addition. 2% hydrochloric acid was added to acidize the mixture to pH=1 after the incubation. The mixture was then washed twice by stirring with water and desolventized to obtain 82.0 g of a crude product of compound B and compound C. Determined by an internal standard method with HPLC, the ratio of compound B to compound C in the crude product was 68:13 and the yield of the mixture of compound B and compound C was 88%.

Example 8

49.3 g of compound A (98%, 0.274 mol), 44.8 g of dichloropyrimidine (98.5%, 0.296 mol), and 203 ml of toluene were added sequentially into a 500 mL three-neck flask, stirred uniformly at room temperature. 0.0137 mol of trimethylamine gas was introduced into the reaction system, cooled to 5° C. with stirring, at which point 55 g (28.87%, 0.294 mol) of a sodium methoxide solution in methanol was added drop-wise, controlling the addition time to be 5 h, and incubated at 10° C. for 5 h after the addition. 2% hydrochloric acid was added to acidize the mixture to pH=1 after the incubation. The mixture was then washed twice by stirring with water and desolventized to obtain 76 g of a crude product of compound B and compound C. Determined by an internal standard method with HPLC, the ratio of compound B to compound C in the crude product was 68:14 and the yield of the mixture of compound B and compound C was 86%.

Example 9

49.3 g of compound A (98%, 0.274 mol), 44.8 g of dichloropyrimidine (98.5%, 0.296 mol), and 203 ml of toluene were added sequentially into a 500 mL three-neck flask, stirred uniformly at room temperature. 0.42 g (having a content of 30%, 0.00213 mol) of a trimethylamine solution in methanol was further added, cooled to 5° C. with stirring. 39 g of methanol was added, and 16.2 g of sodium methoxide solid was added to the flask in 10 equal portions within 5 h (adding 1 equal portion every 30 min), and incubated at 5° C. for 1 h after the addition. 2% hydrochloric acid was added to acidize the mixture to pH=1 after the incubation. The mixture was then washed twice by stirring with water and desolventized to obtain 80 g of a crude product of compound B and compound C. Determined by an internal standard method with HPLC, the ratio of compound B to compound C in the crude product was 70:10 and the yield of the mixture of compound B and compound C was 90%.

Example 10

Based on 10000 g of the acidified wastewater obtained in Example 1 containing 14 g of trimethylamine, 450 g of sodium hydroxide (32%) in liquid form was added to adjust pH to 11. The temperature of the wastewater was raised to 60° C. and the wastewater was then bubbled by introducing a trace amount of nitrogen. The end gas was dried through a drying tower with sodium hydroxide and then absorbed through a three-stage absorption tower with 75 g of methanol to obtain 88.7 g of a methanol solution containing trimethylamine, in which the content of trimethylamine is 15% and the recycling rate of trimethylamine is 95%.

49.3 g of compound A (98%, 0.274 mol), 44.8 g of dichloropyrimidine (98.5%, 0.296 mol), and 203 ml of toluene were added sequentially into a 500 mL three-neck flask, stirred uniformly at room temperature. 0.84 g (having a content of 15%, 0.00213 mol) of the recycled trimethylamine solution in methanol obtained above was further added, cooled to 5° C. with stirring, at which point 55 g (28.87%, 0.294 mol) of a sodium methoxide solution in methanol was added drop-wise, controlling the addition time to be 5 h, and incubated at 5° C. for 1 h after the addition. 2% hydrochloric acid was added to acidize the mixture to pH=1 after the incubation. The mixture was then washed twice by stirring with water and desolventized to obtain 78.9 g of a crude product of compound B and compound C. Determined by an internal standard method with HPLC, the ratio of compound B to compound C in the crude product was 70:10 and the yield of the mixture of compound B and compound C was 89%, showing that good catalytic efficiency and product yield can also achieved by using recycled trimethylamine catalyst.

Comparative Examples 1 to 6

The catalysts used and the molar ratio of catalyst to compound A were shown in the following Table 1, other conditions during the preparation process were the same as Example 1. The yields of the products obtained were shown in the following Table 1.

TABLE 1

| | The names of the catalyst | The ratio of catalyst to compound A | The yield of the mixture of compound B and compound C (%) |
|---|---|---|---|
| Comparative Example 1 | N,N,N,N-tetramethylethylene diamine | 0.00777:1 | 70% |
| Comparative Example 2 | N,N-dimethylpiperazine | 0.00777:1 | 65% |
| Comparative Example 3 | N,N-dimethylpyridine | 0.00777:1 | 20% |
| Comparative Example 4 | N,N-dimethylisopropylamine | 0.00777:1 | 30% |
| Comparative Example 5 | diazabicyclo | 0.00777:1 | 20% |
| Comparative Example 6 | triethylamine | 0.00777:1 | 25% |

It can be seen from Table 1 that the yield of the mixture of compound B and compound C was extremely decreased when replacing the trimethylamine catalyst with a similar basic substance such as triethylamine, diazabicyclo, N,N-dimethylisopropylamine, N,N-dimethylpyridine, N,N-dimethylpiperazine and N,N,N,N-tetramethylethylene diamine under the same conditions. Therefore, the trimethylamine catalyst was specific for the reaction of the present invention and cannot be replaced by other similar basic substances.

Detailed methods of the present invention are illustrated by examples described above in the present invention. However, the present invention is not limited to the detailed methods described above, i.e. it does not mean that the present invention must rely on the detailed methods described above to be implemented. Those skilled in the art should understand that any modifications to the present invention, equivalent replacements of each raw material of the present invention, additions of auxiliary components, selections of specific methods and the like fall within the protection scope and the disclosure scope of the present invention.

The invention claimed is:

1. A preparation method for azoxystrobin intermediates, wherein the preparation method comprises reacting compound A and dichloropyrimidine in the presence of a trimethylamine catalyst with the addition of a sodium methoxide solution in methanol or the addition of sodium methoxide and methanol separately to produce a mixture of azoxystrobin intermediate compound B and compound C, with a reaction equation as following:

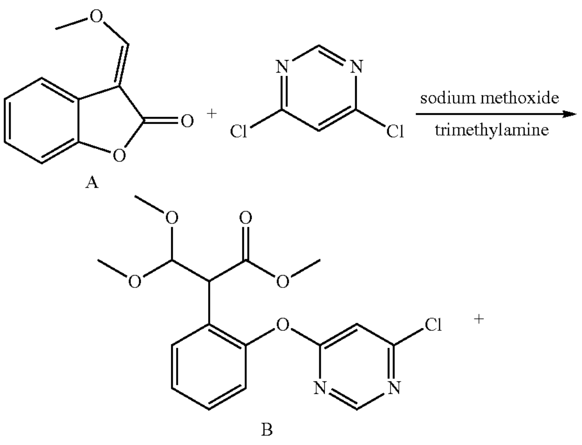

A

B

-continued

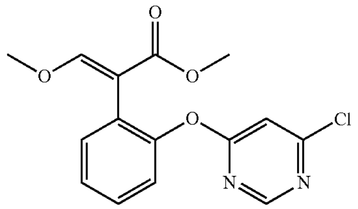

C

2. The preparation method according to claim 1, wherein the trimethylamine catalyst is trimethylamine, a trimethylamine solution, or a salt of trimethylamine.

3. The preparation method according to claim 2, wherein the trimethylamine solution is any one selected from the group consisting of a trimethylamine solution in water, a trimethylamine solution in methanol, a trimethylamine solution in ethanol, a trimethylamine solution isopropanol, a trimethylamine solution in toluene and a trimethylamine solution in xylene, or a combination of at least two selected therefrom.

4. The preparation method according to claim 2, wherein the salt of trimethylamine is any one selected from the group consisting of trimethylamine hydrochloride, trimethylamine sulfate and trimethylamine methanesulfonate, or a combination of at least two selected therefrom.

5. The preparation method according to claim 1, wherein the molar ratio of compound A to the trimethylamine catalyst is 1:0.002 to 1:0.05.

6. The preparation method according to claim 1, wherein the molar ratio of compound A to dichloropyrimidine is 1:1 to 1:1.4.

7. The preparation method according to claim 1, wherein the reaction is performed at a temperature of from −20° C. to 30° C.

8. The preparation method according claim 7, wherein the reaction is performed at a temperature of from 0° C. to 30° C.

9. The preparation method according to claim 1, wherein the reaction is performed for 8-10 h.

10. The preparation method according to claim 1, wherein the preparation method comprises reacting compound A and dichloropyrimidine in the presence of a trimethylamine catalyst with the addition of a sodium methoxide solution in methanol or the addition of sodium methoxide and methanol separately at a temperature of from −20° C. to 30° C. to produce a mixture of azoxystrobin intermediate compound B and compound C, in which the molar ratio of compound A to the trimethylamine catalyst is 1:0.002 to 1:0.05 and the molar ratio of compound A to dichloropyrimidine is 1:1 to 1:1.4.

* * * * *